US012691270B2

(12) United States Patent
Zemansky

(10) Patent No.: US 12,691,270 B2
(45) Date of Patent: Jul. 28, 2026

(54) POWDERED ANTIBIOTIC DISPENSING TOOL DEVICE

(71) Applicant: Stephen Zemansky, Redding, CA (US)

(72) Inventor: Stephen Zemansky, Redding, CA (US)

( * ) Notice: Subject to any disclaimer, the term of this patent is extended or adjusted under 35 U.S.C. 154(b) by 150 days.

(21) Appl. No.: 17/570,440

(22) Filed: Jan. 7, 2022

(65) Prior Publication Data

US 2023/0138321 A1 May 4, 2023

Related U.S. Application Data

(60) Provisional application No. 63/274,268, filed on Nov. 1, 2021.

(51) Int. Cl.
*A61M 35/00* (2006.01)

(52) U.S. Cl.
CPC ..... *A61M 35/003* (2013.01); *A61M 2202/064* (2013.01); *A61M 2205/6009* (2013.01); *A61M 2205/6081* (2013.01)

(58) Field of Classification Search
CPC .......... A61J 7/0007; A61J 17/00; A61J 19/00; A61J 43/26; A61M 13/00; A61M 15/0028; A61M 15/0036; A61M 15/0061; A61M 2202/064; A61M 2205/6009; A61M 2205/6081; A61M 2205/7545; A61M 35/00; A61M 35/003; A61M 35/006; A61M 11/00
See application file for complete search history.

(56) References Cited

U.S. PATENT DOCUMENTS

| | | | | | |
|---|---|---|---|---|---|
| 4,568,331 | A | * | 2/1986 | Fischer | A61J 7/0046 604/518 |
| 5,478,311 | A | * | 12/1995 | Klearman | A61J 7/0007 604/82 |
| 2004/0050885 | A1 | * | 3/2004 | Stradella | A61M 15/0028 222/633 |
| 2008/0078382 | A1 | * | 4/2008 | LeMahieu | A61M 16/0069 128/200.24 |
| 2016/0058662 | A1 | * | 3/2016 | Wheeler | A61J 1/10 206/530 |
| 2016/0375202 | A1 | * | 12/2016 | Goodman | A61L 26/0023 |
| 2018/0333332 | A1 | * | 11/2018 | Abusbeih | A61J 7/0007 |
| 2021/0378915 | A1 | * | 12/2021 | Yang | A61J 7/0007 |
| 2022/0226196 | A1 | * | 7/2022 | Hadad | A61M 5/3295 |

* cited by examiner

*Primary Examiner* — Andrew J Mensh
*Assistant Examiner* — Jihad Dakkak
(74) *Attorney, Agent, or Firm* — Brennan, Manna & Diamond, LLC

(57) ABSTRACT

The present invention relates to the field of medical dispensing tools. More specifically, the present invention relates to a powdered antibiotic dispensing tool device that is comprised of a body having a top plate and a bottom plate, and a stem that attaches to the bottom plate, wherein the stem further has at least two handles. The device further preferably resembles a syringe, comprised of an accordion-like body that is flexible or semi-flexible, such that it can expand and contract. The device is also comprised of a stem that allows a user to easily grip the device to crush an antibiotic into a powder and administer the antibiotic by spraying it through the end of the stem. In this manner, the device can be applied to any antibiotic such that it may be turned into a powder and sprayed on a surgical site or wound to prevent infection.

4 Claims, 3 Drawing Sheets

POWDERED ANTIBIOTIC DISPENSING TOOL DEVICE

CROSS-REFERENCE TO RELATED APPLICATION

The present application claims priority to, and the benefit of, U.S. Provisional Application No. 63/274,268, which was filed on Nov. 1, 2021 and is incorporated herein by reference in its entirety.

FIELD OF THE INVENTION

The present invention relates generally to the field of medical dispensing tools. More specifically, the present invention relates to a powdered antibiotic dispensing tool device that is comprised of a body having a top plate, a bottom plate and a stem that attaches to the bottom plate, wherein the stem further has at least two handles. The device further preferably resembles a syringe comprised of an accordion-like body that is flexible or semi-flexible, such that it can expand and contract. The device is also comprised of a stem that allows a user to easily grip the device to both crush an antibiotic into a powder and administer the antibiotic by spraying it through the end of the stem. In this manner, the device can be applied to any antibiotic, such that it may be turned into a powder and sprayed on a surgical site or wound to prevent infection. Accordingly, the present disclosure makes specific reference thereto. Nonetheless, it is to be appreciated that aspects of the present invention are also equally applicable to other like applications, devices and methods of manufacture.

BACKGROUND

Powdered antibiotics are typically difficult to keep sterile. Medical professionals may lack the means to get powdered antibiotics delivered to a patient without contamination. If the antibiotic does not remain sterile, there is a high chance of site infection, whether it be on a surgical site or wound. Within the sterile field of a medical procedure, medications are not allowed to be mixed, as it would result in a broken sterile field. Thus, keeping medications from cross-contaminating with one another is of high importance. Technology currently used to deliver powdered antibiotics to patients is not convenient or effective, as it is difficult to prevent cross-contamination.

Therefore, there exists a long-felt need in the art for an improved powdered antibiotic dispensing tool device. There also exists a long-felt need in the art for a powdered antibiotic dispensing tool device that can administer powdered antibiotics in a sterile field without contamination occurring. Further, there exists a long-felt need in the art for a powdered antibiotic dispensing tool device that can be labeled to ensure the proper medication gets delivered to the patient. In addition, there exists a long-felt need in the art for a powdered antibiotic dispensing tool device that can crush antibiotics such that the antibiotics can be evenly distributed over a surgical site or wound in a powdered form.

The subject matter disclosed and claimed herein, in one embodiment thereof, comprises a powdered antibiotic dispensing tool device. The device is comprised of a body having a top plate, a bottom plate and a stem that attaches to the bottom plate, wherein the stem further comprises at least two handles. The device preferably resembles a syringe comprised of an accordion-like body that is flexible or semi-flexible, such that it can expand and contract. The device is also comprised of a stem that allows a user to easily grip the device to both crush an antibiotic into a powder and administer the antibiotic by spraying it through the end of the stem. In this manner, the device can be applied to any antibiotic such that it may be turned into a powder and sprayed on a surgical site or wound to prevent infection.

In this manner, the powdered antibiotic dispensing tool device of the present invention accomplishes all the forgoing objectives and provides an improved means to administer powdered antibiotics. Further, the device can crush antibiotic clusters into a fine-grain powder such that the antibiotic may be sprayed evenly over a surgical site or wound. In addition, the device is comprised of a labeling system that ensures the correct medication gets delivered to the patient without any contamination or break of the sterile field.

SUMMARY

The following presents a simplified summary in order to provide a basic understanding of some aspects of the disclosed innovation. This summary is not an extensive overview, and it is not intended to identify key/critical elements or to delineate the scope thereof. Its sole purpose is to present some general concepts in a simplified form as a prelude to the more detailed description that is presented later.

The subject matter disclosed and claimed herein, in one embodiment thereof, comprises a powdered antibiotic dispensing tool device. The device is primarily comprised of a body having a top plate, a bottom plate and a stem that attaches to the bottom plate, wherein the stem further has at least two handles. In differing embodiments, the device may have the appearance of a syringe. In the preferred embodiment, the body of the device has an accordion-like appearance that allows the body to expand and contract. The body may also be made of a plurality of materials commonly used for making medical devices. However, the body is preferably made of a flexible or semi-flexible plastic material. In addition, any surface of the body may be comprised of a plurality of indicia such as patterns, logos, emblems, images, symbols, designs, letters, words, characters, animals, advertisements, brands, etc., that may or may not be medically-related.

The body also has an interior cavity capable of crushing antibiotics into a powdered form. A top plate and a bottom plate that abut the interior cavity are movable, such that the interior cavity can expand and contract. The top and bottom plates are made of a rigid plastic or metal material, such that they can squeeze together to effectively powder antibiotics. At least one agitator may protrude from the inner surface of the top plate to powder the antibiotic more efficiently. A continuous opening can be found in the bottom plate to allow the powdered antibiotic to exit the internal cavity of the body. In addition, an antibiotic that does not need to be crushed (wherein said antibiotic has already been powdered) may also be used in the device.

A hollow stem is fixedly or removably-attached to the bottom surface of the bottom plate, such that a continuous opening at a first end of the stem accepts the powdered antibiotic leaving the body. A second end of the stem also has a continuous opening that allows the powdered antibiotic to be sprayed onto a patient. In addition, at least two handles are fixedly-attached to the second end of the stem that allow a user to grip two fingers around the stem. By additionally placing a thumb on the outer surface of the top plate, the accordion-like body can be contracted together to crush an antibiotic or administer a powdered antibiotic. A cap may be placed over the continuous opening at the second end of the stem to prevent the powdered antibiotic from falling out during the powdering process. Further, in one potential embodiment, the cap may have a labeling system, such as color coding, labels, abbreviation or another form of indicia, that indicates the medication present in the device to ensure proper treatment. Once the antibiotic is ready to be administered, the cap may be taken off and the fingers and thumb of a user may work to contract the body of the device and administer the medicine to a patient.

Accordingly, the powdered antibiotic dispensing tool device of the present invention is particularly advantageous, as it allows a medical professional to administer powdered antibiotics evenly to a patient. Further, the device is comprised of a labeling system that ensures the correct medication gets delivered to the patient. In addition, the device can crush antibiotic clusters into a fine-grain powder, such that the antibiotic can be sprayed over a surgical site or wound without any contamination or break of the sterile field. In this manner, the powdered antibiotic dispensing tool device overcomes the limitations of existing methods of dispensing powdered medication known in the art.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and are intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION

Figure 1:
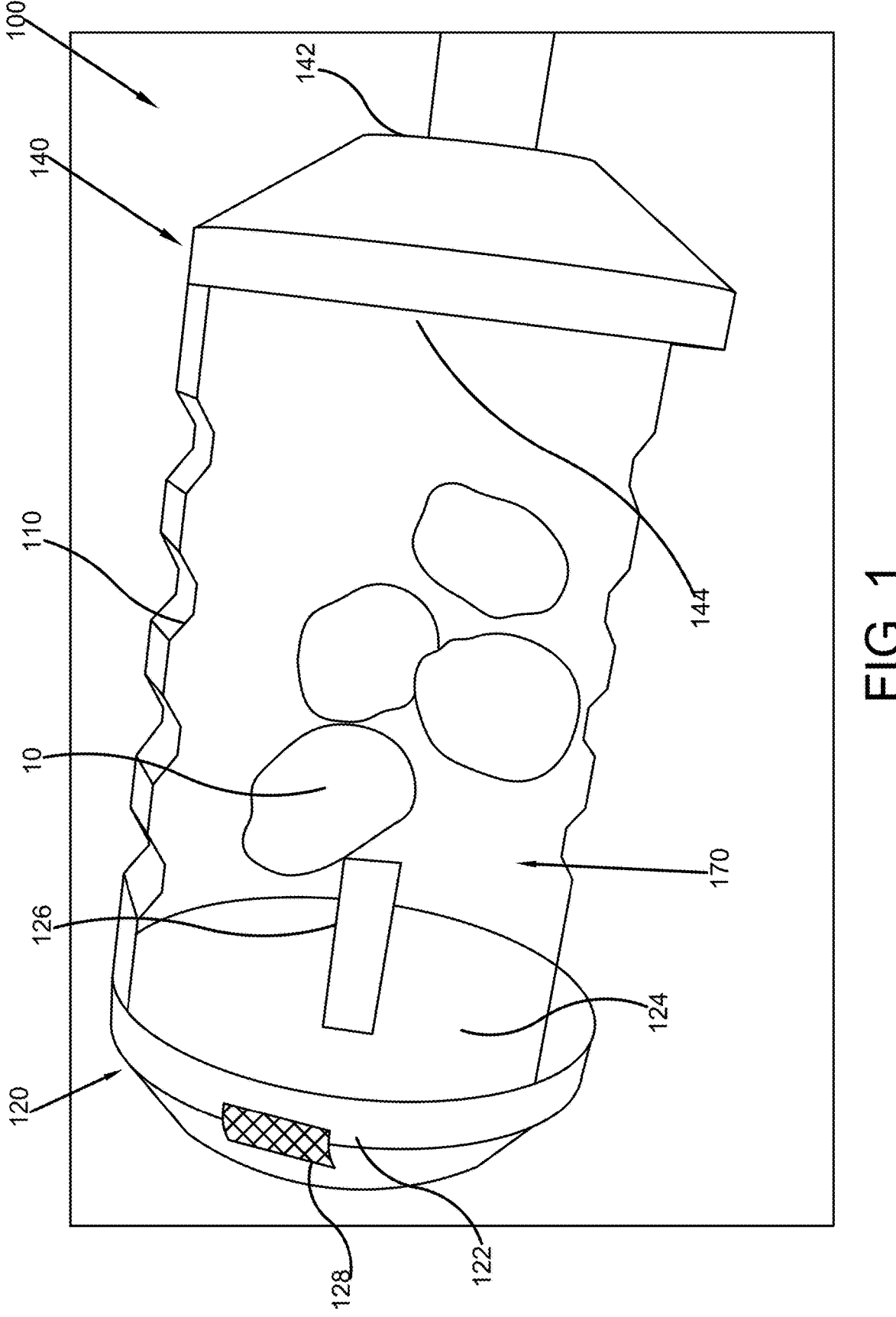
FIG. 1 illustrates a perspective and partially cross-sectional view of one potential embodiment of a powdered antibiotic dispensing tool device of the present invention while in a fully expanded position in accordance with the disclosed architecture.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof. Various embodiments are discussed hereinafter. It should be noted that the figures are described only to facilitate the description of the embodiments. They are not intended as an exhaustive description of the invention, and do not limit the scope of the invention. Additionally, an illustrated embodiment need not have all the aspects or advantages shown. Thus, in other embodiments, any of the features described herein from different embodiments may be combined.

As noted above, there is a long-felt need in the art for an improved powdered antibiotic dispensing tool device. There also exists a long-felt need in the art for a powdered antibiotic dispensing tool device that can administer powdered antibiotics in a sterile field without contamination occurring. Further, there exists a long-felt need in the art for a powdered antibiotic dispensing tool device that can be labeled to ensure the proper medication gets delivered to the patient. In addition, there exists a long-felt need in the art for a powdered antibiotic dispensing tool device can crush antibiotic clusters, such that the antibiotic can be evenly distributed over a surgical site or wound.

The present invention, in one exemplary embodiment, is comprised of a powdered antibiotic dispensing tool device that allows a medical professional to distribute a powdered antibiotic safely and evenly onto a surgical site or wound without contamination. The device is primarily comprised of a body having a top plate, a bottom plate and a stem that attaches to the bottom plate, wherein the stem further has at least two handles. In differing embodiments, the body may have the appearance of a syringe, and in the preferred embodiment the body has an accordion-like appearance that allows it to contract and expand. The body may also be made of a plurality of materials that may be commonly used for making medical devices, but is preferably made of a flexible or semi-flexible plastic material. In addition, any surface of the body may be comprised of a plurality of indicia such as patterns, logos, emblems, images, symbols, designs, letters, words, characters, animals, advertisements, brands, etc., that may or may not be medically-related.

Further, the body has an interior cavity where antibiotics may be placed. A top plate and a bottom plate make up the extents of the interior cavity, and are movable such that an antibiotic can be crushed into a powdered form by pressing the top and bottom plates together. Both the top and bottom plates may be made of a rigid plastic or metal in differing embodiments to effectively powder the antibiotics. The top plate is comprised of an outer surface and an inner surface. In one potential embodiment, the outer surface of the top plate may be comprised of a textured grip that allows the user to powder antibiotics more effectively. The inner surface of the top plate gets pressed down into the bottom plate to powder antibiotics. However, in another potential embodiment, the inner surface of the top plate may be comprised of at least one agitator that helps powder the antibiotics more efficiently. The bottom plate is further comprised of a bottom surface and an inner surface. A continuous opening runs through both the inner surface and the bottom surface of the bottom plate to allow the powdered antibiotic to exit the device. In differing embodiments, the top plate may contract towards a fixed bottom plate, the bottom plate may contract towards a fixed top plate, or both the top plate and bottom plate may be free to move towards each other axially along the length of the body. In addition, pre-powdered antibiotics may also be placed in the interior cavity of the body to be dispensed onto a patient.

A hollow stem is attached to the bottom surface of the bottom plate. The stem may be fixedly attached, or it may be removable such that it can be easily replaced to maintain a sterile field in medical procedures. A first end of the stem is comprised of a continuous opening in line with the continuous opening of the bottom plate that allows the transfer of a powdered antibiotic from the internal cavity of the body to the stem. A second end of the stem is further comprised of at least two handles and a continuous opening. The handles are fixedly-attached to both sides of the stem such that a user can place his or her fingers onto a top edge of the handles and a thumb or other body part on the outer surface of the top plate and press together to collapse the accordion-like body. In one potential embodiment, the handles may be comprised of a textured grip to aid in crushing the antibiotics. The continuous opening of the second end of the stem allows the powdered antibiotic to exit the device such that it can be sprayed on a wound. Further, a cap may cover the continuous opening of the second end of the stem to prevent the powdered antibiotic from falling out.

In one potential embodiment, the cap may have a labeling system, such as color coding, labels, abbreviation or another form of indicia, that indicates the medication present in the device to ensure proper treatment. To crush the antibiotics, the cap may be placed over the continuous opening of the second end of the stem to prevent any of the powdered antibiotic from escaping the device prematurely. Then, when the antibiotic is completely powdered and ready to be administered to the patient, the cap may be removed so the contraction of the accordion-like body may push the powdered antibiotic out of the body, through the stem and onto the wound or surgical site of a patient.

Accordingly, the powdered antibiotic dispensing tool device of the present invention is particularly advantageous as it allows a medical professional to administer powdered antibiotics evenly to a patient. Further, the device can crush antibiotics into a powder, such that the antibiotic may be sprayed over a surgical site or wound. In addition, the device is comprised of a labeling system that indicates the medication present in the device to ensure proper treatment without contamination or a break of the sterile field.

Referring initially to the drawings, FIG. 1 illustrates a perspective view of one potential embodiment of a powdered antibiotic dispensing tool device 100 of the present invention while in a fully expanded position in accordance with the disclosed architecture. The device 100 is primarily comprised of a body 110 having a top plate 120, a bottom plate 140 and a stem 150 that attaches to the bottom plate 140, wherein the stem 150 further comprises at least two handles 158. In differing embodiments, the body 110 may have an accordion-like appearance, such that the body 110 may contract and expand to both crush antibiotics 10 into a powdered form within the body 110 and then administer said antibiotics 10 to a wound site 20. Further, the body 110 or certain components of the body 110 may be made of a plurality of materials such as metal, but the body 110 is preferably made of a flexible or semi-flexible plastic such as, but not limited to, acrylic, polycarbonate, polyethylene, thermoplastic, acrylonitrile butadiene styrene, low density polyethylene, medium density polyethylene, high density polyethylene, polyethylene terephthalate, polyvinyl chloride, polystyrene, polylactic acid, acetal, nylon, fiberglass, etc. In addition, the body 110 may be transparent, semitransparent or opaque in differing embodiments. Furthermore, any surface 122, 124, 142, 144 of the body 110 may be comprised of any number of indicia 200 in the form of patterns, logos, emblems, images, symbols, designs, letters, words, characters, animals, advertisements, brands, etc. that may or may not be medically-related.

Figure 2:
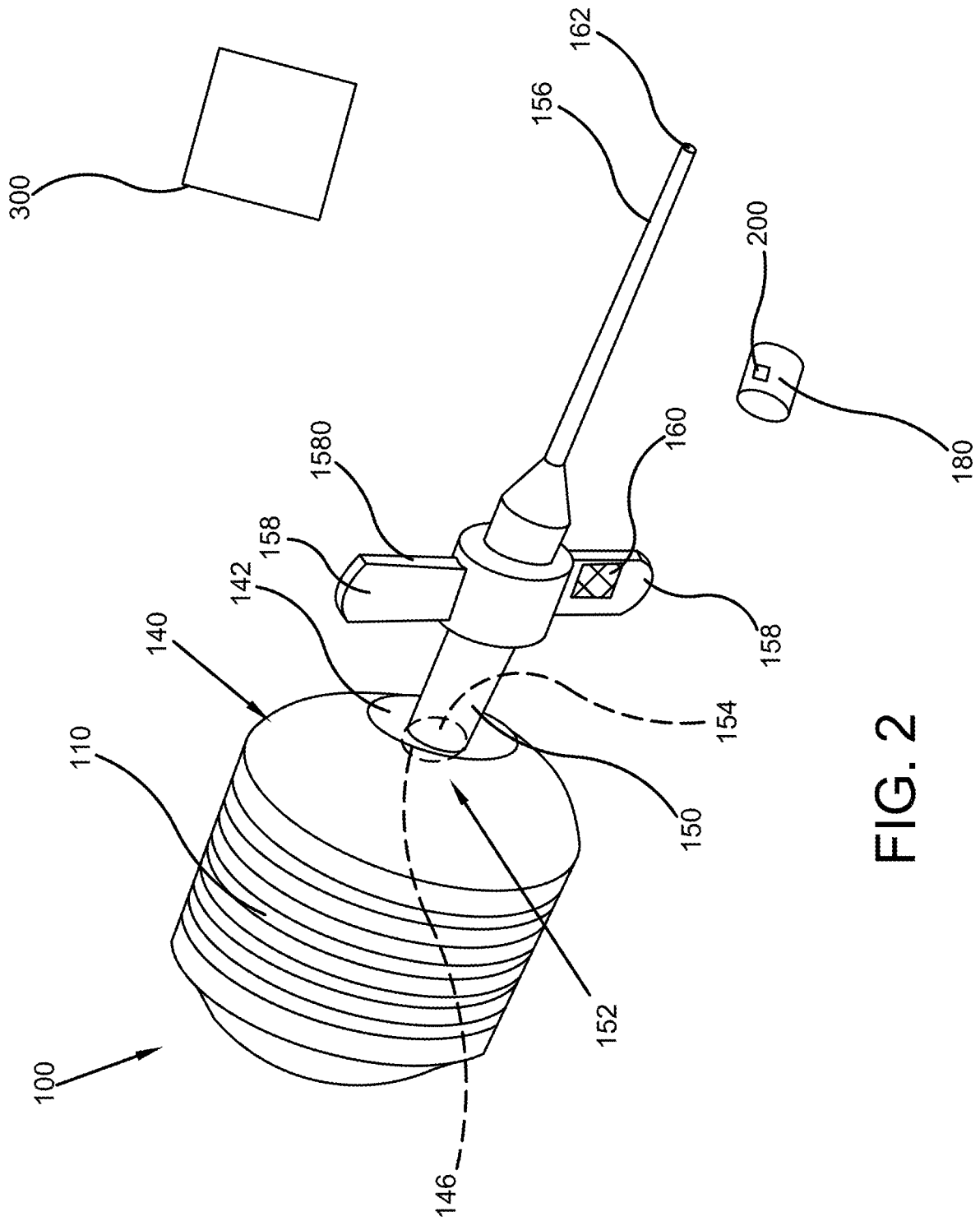
FIG. 2 illustrates a perspective view of one potential embodiment of a powdered antibiotic dispensing tool device of the present invention while in a fully contracted position in accordance with the disclosed architecture.
Figure 3:
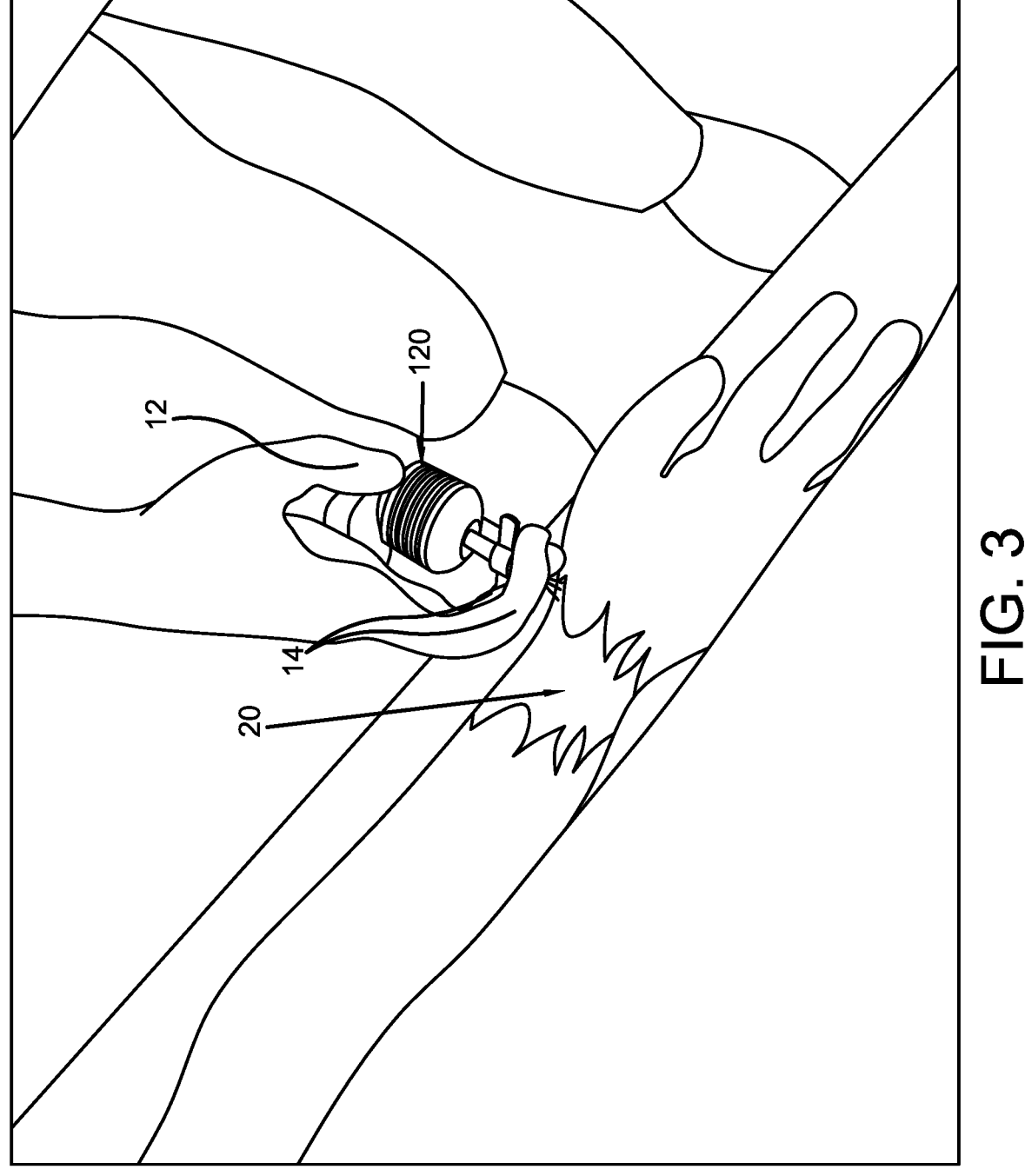
FIG. 3 illustrates a perspective view of one potential embodiment of a powdered antibiotic dispensing tool device of the present invention while in a fully contracted position while being held by a user in accordance with the disclosed architecture.

In the preferred embodiment of the device 100 shown in FIGS. 1, 2, and 3, the body 110 has a generally accordion-like appearance. The body 110 is further comprised of an internal cavity 170 in which antibiotics 10 may be placed and then crushed into a powder and administered to a surgical site or wound site 20 of a patient. The body 110 is further comprised of a top plate 120 and a bottom plate 140. In differing embodiments, both the top and bottom plates 120, 140 may be made of a plurality of materials such as a rigid plastic, but are preferably made of a durable metal to efficiently break down antibiotics 10 into a powdered form. The top plate 120 is further comprised of an outer surface 122 and an inner surface 124. In one potential embodiment, the outer surface 122 of the top plate 120 may be comprised of a grip area 128 which may be textured with knurling, protrusions, material, etc., to aid in gripping and using the device 100. In another potential embodiment, the inner surface 124 of the top plate 120 may be comprised of at least one agitator 126 that helps break down antibiotics 10 into a powdered form more efficiently.

The bottom plate 140 is also comprised of two surfaces, a bottom surface 142 and an inner surface 144. A continuous opening 146 runs through the bottom plate 140 to allow powdered antibiotic 10 to be expelled from the internal cavity 170 of the body 110. In differing embodiments, a movable top plate 120 may contract towards a fixed bottom plate 140, a movable bottom plate 140 may contract towards a fixed top plate 120, or both the top plate 120 and bottom plate 140 may both be movable and be pushed towards one another to crush antibiotics 10 into a powdered form and then expel said antibiotics through the hollow stem 150 and onto a wound site 20. In addition, pre-powdered antibiotics 10 may be placed in the device 100 to be dispensed evenly onto a patient in the same manner (as best seen in FIG. 3).

FIG. 2 illustrates a perspective view of one potential embodiment of a powdered antibiotic dispensing tool device 100 of the present invention while in a fully contracted position in accordance with the disclosed architecture. A hollow stem 150 made from the same material as the bottom plate 140 is attached to the bottom surface 142 of the bottom plate 140. The stem 150 may be fixedly-attached to the bottom surface 142, or the stem 150 may be removably-attached, such that it can easily be disposed of and replaced to maintain a sterile field and reduce the possibility of contamination. A first end 152 of the stem 150 is comprised of a continuous opening 154 concentric with and of the same size and shape as the continuous opening 146 of the bottom plate 140. The continuous opening 154 allows powdered antibiotic 10 to be expelled from the internal cavity 170 of the body 110 to the stem 150 by performing the motions described supra with respect to the top plate 120 and bottom plate 140. A second end 156 of the stem 150 is further comprised of at least two handles 158 and a continuous opening 162. The handles 158 are fixedly-attached to both sides of the stem 150 such that a user can comfortably place two fingers 14 onto a top edge 1580 of the handles 158, with one finger 14 on each handle 158. By additionally pressing a thumb 12 or other body part on the outer surface 122 of the top plate 120, a user can contract and expand the accordion-like body 110 to crush antibiotics 10 into a powdered form and then administer antibiotics 10. In one potential embodiment, a grip 160, possibly textured with knurling, protrusions, material, etc., may cover the handles 158 to aid in crushing and administering the antibiotics 10. The continuous opening 162 of the second end 156 of the stem 150 allows the powdered antibiotic 10 to exit the device 100 such that it can be sprayed on a wound or surgical site 20 of a patient.

In another potential embodiment, the continuous opening 162 of the second end 156 of the stem 150 may be further comprised of a removable cap 180. Further, in one potential embodiment, the cap 180 may have a labeling system, such as color coding, labels, abbreviation or another form of indicia 200, that indicates the type of antibiotic/medicine 10 present in the device 100 to ensure proper treatment (e.g. the proper medicine is used on the proper patient). This system can then be crossed referenced or coincide with existing labeling systems known in the medical field and may also include an identification chart 300 that explains the labeling system of each cap 180. The cap 180 may be placed over the second end 156 when the antibiotic 10 is being crushed into powder within the body 110 to prevent said antibiotic 10 from exiting the body 110 via the stem 150. Once the antibiotic 10 is a fine-grain powder and ready to be administered to the patient, the cap 180 may be removed from the second end 156 of the stem 150. Using two fingers 14 on the handles 158 of the stem 150 and a thumb 12 on the outer surface 122 of the top plate 120, a user may contract the accordion-like body 110 to spray the powdered antibiotic 10 safely and evenly onto a patient, as described supra.

Certain terms are used throughout the following description and claims to refer to particular features or components. As one skilled in the art will appreciate, different persons may refer to the same feature or component by different names. This document does not intend to distinguish between components or features that differ in name but not structure or function. As used herein "powdered antibiotic dispensing tool device" and "device" are interchangeable and refer to the powdered antibiotic dispensing tool device 100 of the present invention.

Notwithstanding the forgoing, the powdered antibiotic dispensing tool device 100 of the present invention and its various components can be of any suitable size and configuration as is known in the art without affecting the overall concept of the invention, provided that they accomplish the above-stated objectives. One of ordinary skill in the art will appreciate that the size, configuration and material of the powdered antibiotic dispensing tool device 100 as shown in the FIGS. are for illustrative purposes only, and that many other sizes and shapes of the powdered antibiotic dispensing tool device 100 are well within the scope of the present disclosure. Although the dimensions of the powdered antibiotic dispensing tool device 100 are important design parameters for user convenience, the powdered antibiotic dispensing tool device 100 may be of any size, shape and/or configuration that ensures optimal performance during use and/or that suits the user's needs and/or preferences.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A powdered antibiotic dispensing tool device comprising:
   an accordion-like body further comprised of:
   a top plate comprising an inner surface and an exterior surface comprising a top plate textured grip;
   an agitator on the inner surface of the top plate;
   a bottom plate;
   a hollow stem;
   at least two handles each having a textured grip area; and
   an interior cavity;
   an antibiotic housed in the interior cavity;
   a cap; and
   an identification chart; and
   wherein the hollow stem is removably attachable to the bottom plate;
   wherein the accordion-like body is configured to collapse when the top plate and bottom plates are pushed inward;
   wherein the antibiotic is crushed into a powdered-form by pushing the top plate and the bottom plate together to collapse the accordion-like body; and
   wherein the accordion-like body is transparent.

2. The powdered antibiotic dispensing tool device of claim 1 further comprising a labeling system that identifies the antibiotic.

3. The powdered antibiotic dispensing tool device of claim 2, wherein the identification chart explains the labeling system.

4. The powdered antibiotic dispensing tool device of claim 1, wherein the bottom plate is repositionable in the direction of the top plate which is fixed.

* * * * *